United States Patent [19]

Stetter et al.

[11] Patent Number: 4,772,309
[45] Date of Patent: Sep. 20, 1988

[54] 5-ACYLAMINO-PYRAZOLES, COMPOSITION CONTAINING THEM, AND HERBICIDAL AND PLANT GROWTH REGULATING METHOD OF USING THEM

[75] Inventors: Jörg Stetter; Reinhold Gehring, both of Wuppertal; Otto Schallner, Monheim; Hans-Joachim Santel, Leverkusen; Robert R. Schmidt; Klaus Lürssen, both of Bergisch-Gladbach, all of Fed. Rep. of Germany

[73] Assignee: Bayer Aktiengesellschaft, Leverkusen, Fed. Rep. of Germany

[21] Appl. No.: 27,756

[22] Filed: Mar. 19, 1987

[30] Foreign Application Priority Data

Mar. 21, 1986 [DE] Fed. Rep. of Germany ....... 3609542

[51] Int. Cl.$^4$ .................... A61K 43/56; A61K 43/82; C07D 403/12; C07D 419/12
[52] U.S. Cl. .......................................... 71/92; 71/90; 71/91; 71/93; 544/2; 544/5; 544/8; 544/54; 544/58.4; 544/58.5; 544/58.6; 544/65; 544/66; 544/67; 544/68; 544/96; 544/98; 544/131; 544/140; 544/182; 544/215; 544/219; 544/238; 544/298; 544/300; 544/310; 544/316; 544/317; 544/319; 544/364; 544/371; 544/405; 546/193; 546/194; 546/211; 546/256; 546/279; 548/122; 548/123; 548/124; 548/125; 548/127; 548/128; 548/129; 548/131; 548/132; 548/134; 548/135; 548/136; 548/143; 548/144; 548/182; 548/183; 548/187; 548/188; 548/213; 548/214; 548/215; 548/225; 548/226; 548/227; 548/228; 548/229; 548/230; 548/232; 548/235; 548/237; 548/238; 548/239; 548/240; 548/243; 548/247; 548/248; 548/249; 548/255; 548/262; 548/263; 548/265; 548/269; 548/336; 548/362; 548/374
[58] Field of Search ............... 548/362, 374, 122, 123, 548/124, 125, 127, 128, 129, 131, 132, 134, 135, 136, 143, 144, 182, 183, 187, 188, 213, 214, 215, 225, 226, 227, 228, 229, 230, 232, 235, 237, 238, 239, 240, 243, 247, 248, 249, 255, 262, 263, 265, 336, 362, 374; 71/92, 90, 91, 93; 544/2, 5, 8, 54, 58.4, 58.5, 58.6, 65, 66, 67, 68, 96, 98, 131, 140, 182, 215, 219, 238, 298, 300, 310, 316, 317, 319, 364, 371, 405; 546/193, 194, 211, 256, 279

[56] References Cited

FOREIGN PATENT DOCUMENTS 0154115 9/1985 European Pat. Off. ................ 71/92
3226513 2/1983 Fed. Rep. of Germany ...... 548/362
3213575 3/1983 Fed. Rep. of Germany .......... 71/92

Primary Examiner—Mary C. Lee
Assistant Examiner—Kurt G. Briscoe
Attorney, Agent, or Firm—Sprung Horn Kramer & Woods

[57] ABSTRACT

A 5-Acylamino-pyrazole derivatives of the formula

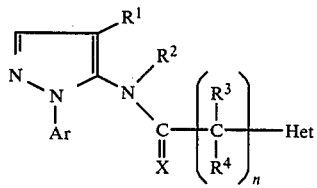

in which
$R^1$ represents hydrogen, halogen or nitro,
$R^2$ represents hydrogen, alkyl, alkenyl, alkinyl or optionally substituted cycloalkyl,
$R^3$ represents hydrogen or alkyl,
$R^4$ represents hydrogen or alkyl,
X represents oxygen or sulphur,
n represents the integer 0, 1 or 2,
Ar represents in each case optionally substituted phenyl or pyridyl and
Het represents an optionally substituted 5- or 6- membered heterocyclic radical linked via a carbon atom,
which exhibit herbicidal and plant growth regulating activity.

15 Claims, No Drawings

5-ACYLAMINO-PYRAZOLES, COMPOSITION CONTAINING THEM, AND HERBICIDAL AND PLANT GROWTH REGULATING METHOD OF USING THEM

The invention relates to new 5-acylamino-pyrazole derivatives, several processes for their preparation and their use as herbicides and growth regulators.

It is already known that certain 5-acylamino-1-aryl-pyrazoles, such as, for example, 4-cyano-5-propionamido-1-(2,4,6-trichlorophenyl)-pyrazole (compare DE-OS No. (German Published Specification) 3,226,513) have herbicidal properties.

However, the herbicidal activity of these already known compounds against weeds, like their tolerance towards important crop plants, is not always completely satisfactory in all fields of use.

New 5-acylamino-pyrazole derivatives of the general formula (I)

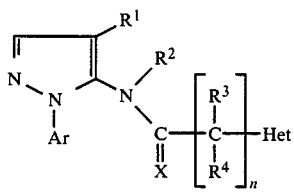

in which $R^1$ represents hydrogen, halogen or nitro,
$R^2$ represents hydrogen, alkyl, alkenyl, alkinyl or optionally substituted cycloalkyl,
$R^3$ represents hydrogen or alkyl,
$R^4$ represents hydrogen or alkyl,
X represents oxygen or sulphur,
n represents the integers 0, 1 or 2,
Ar represents in each case optionally substituted phenyl or pyridyl and
Het represents an optionally substituted 5- or 6-membered heterocyclic radical linked via a carbon atom, have been found.

It has furthermore been found that the new 5-acylamino-pyrazole derivatives of the formula (I)

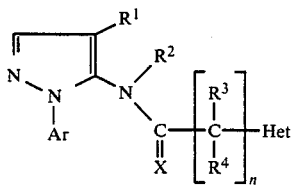

in which $R^1$ represents hydrogen, halogen or nitro,
$R^2$ represents hydrogen, alkyl, alkenyl, alkinyl or optionally substituted cycloalkyl,
$R^3$ represents hydrogen or alkyl,
$R^4$ represents hydrogen or alkyl,
X represents oxygen or sulphur,
n represents the integers 0, 1 or 2,
Ar represents in each case optionally substituted phenyl or pyridyl and
Het represents an optionally substituted 5- or 6-membered heterocyclic radical linked via a carbon atom, are obtained with the aid of the processes described below:

(a) 5-Acylamino-pyrazole derivatives of the formula (Ia)

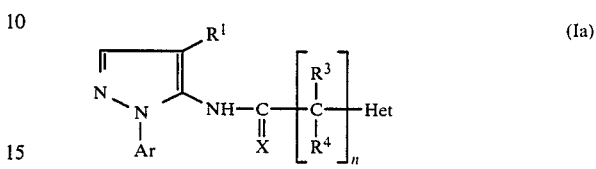

in which $R^1$, $R^3$, $R^4$, X, Ar, Het and the index n have the abovementioned meaning, are obtained by a process in which 5-amino-1-aryl-pyrazoles of the formula (II)

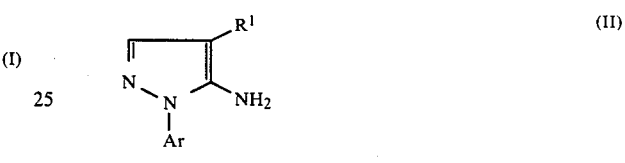

in which
$R^1$ and Ar have the abovementioned meaning, are reacted with acylating agents of the formula (III)

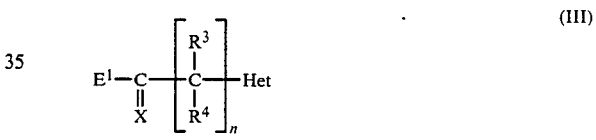

in which
X, $R^3$, $R^4$, Het and the index n have the abovementioned meaning and
$E^1$ represents an electron-withdrawing leaving group, if appropriate in the presence of a diluent, if appropriate in the presence of an acid-binding agent and if appropriate in the presence of a catalyst;

(b) 5-Acylamino-pyrazole derivatives of the formula (Ib)

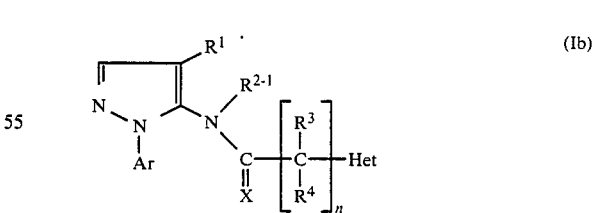

in which
$R^1$, $R^3$, $R^4$, X, Ar, Het and the index n have the abovementioned meaning and
$R^{2-1}$ represents alkyl, alkenyl, alkinyl or optionally substituted cycloalkyl, are obtained by a process in which the 5-acylamino-pyrazole derivatives obtainable by process (a) of the formula (Ia)

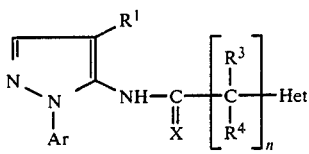

in which

R$^1$, R$^3$, R$^4$, X, Ar, Het and the index n have the abovementioned meaning, are reacted with reagents of the formula (IV)

 (IV)

in which

R$^{2-1}$ has the abovementioned meaning and

E$^2$ represents halogen, or represents optionally substituted alkoxysulphonyloxy, or represents optionally substituted arylsulphonyloxy, if appropriate in the presence of a diluent and if appropriate in the presence of an acid-binding agent, and if appropriate in the presence of a catalyst;

(c) 5-Acylamino-pyrazole derivatives of the formula (Ic)

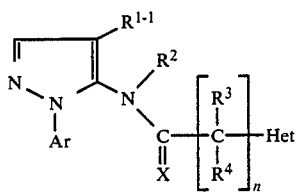

in which

R$^2$, R$^3$, R$^4$, X, Ar, Het and the index n have the abovementioned meaning and R$^{1-1}$ represents halogen or nitro, are alternatively also obtained by a process in which the 5-acylamino-pyrazole derivatives obtainable with the aid of processes (a) or (b), of the formula (Id)

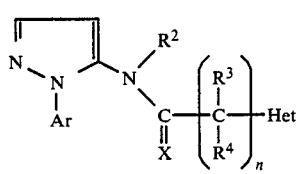

in which

R$^2$, R$^3$, R$^4$, X, Ar, Het and the index n have the abovementioned meaning, are reacted with halogenating or nitrating agents of the formula (V)

 (V)

in which

R$^{1-1}$ has the abovementioned meaning and

E$^3$ represents an electron-withdrawing leaving group, if appropriate in the presence of a diluent and if appropriate in the presence of a catalyst or reaction auxiliary.

Finally, it has been found that the new 5-acylamino-pyrazole derivatives of the general formula (I) have herbicidal properties, and in particular also selective herbicidal properties, and plant growth-regulating properties.

Surprisingly, the 5-acylamino-pyrazole derivatives of the general formula (I) according to the invention exhibit a considerably better general herbicidal activity against problem weeds which are difficult to combat and at the same time a clearly improved tolerance towards important crop plants, such as, in particular, soy beans and wheat, in comparison with the 5-acylamido-1-aryl-pyrazoles known from the prior art, such as, for example, 4-cyano-5-propionamido-1-(2,4,6-trichlorophenyl)pyrazole, which is a closely related compound chemically and from the point of view of its action.

Formula (I) provides a general definition of the 5-acylamino-pyrazole derivatives according to the invention. Preferred compounds of the formula (I) are those in which R$^1$ represents hydrogen, nitro, fluorine, chlorine, bromine or iodine;

R$^2$ represents hydrogen, or represents straight-chain or branched alkyl with 1 to 12 carbon atoms, or represents straight-chain or branched alkenyl or alkinyl with in each case 3 to 8 carbon atoms, or represents cycloalkyl which has 3 to 8 carbon atoms and is optionally monosubstituted or disubstituted by identical or different substituents, substituents which may be mentioned being halogen and alkyl with 1 to 4 carbon atoms;

R$^3$ represents hydrogen, or represents straight-chain or branched alkyl with 1 to 6 carbon atoms;

R$^4$ represents hydrogen, or represents straight-chain or branched alkyl with 1 to 6 carbon atoms;

X represents oxygen or sulphur;

n represents the integer 0, 1 or 2;

Ar represents phenyl which is optionally monosubstituted or polysubstituted by identical or different substituents, or represents 2-pyridyl, 3-pyridyl or 4-pyridyl, in each case optionally monosubstituted or polysubstituted by identical or different substituents, possible substituents on the phenyl and the pyridyl being: cyano, nitro, halogen, in each case straight-chain or branched alkyl, alkoxy and alkoxycarbonyl with in each case 1 to 4 carbon atoms in the alkyl part and also in each case straight-chain or branched halogenoalkyl and halogenoalkoxy with in each case 1 to 4 carbon atoms and 1 to 9 identical or different halogen atoms, and a radical —S(O)$_m$—R$^5$, wherein R$^5$ represents amino, or represents in each case straight-chain or branched alkyl, alkylamino, dialkylamino or halogenoalkyl with in each case 1 to 4 carbon atoms in the individual alkyl parts and, in the case of the halogenoalkyl, with 1 to 9 identical or different halogen atoms, and m represents the integer 0, 1 or 2; and Het represents a 5- or 6-membered unsaturated, partly saturated or saturated heterocyclic radical which has one to three identical or different hetero atoms (oxygen, nitrogen or sulphur), is optionally monosubstituted, disubstituted or trisubstituted by identical or different substituents and is linked via a carbon atom, substituents which may be mentioned being: halogen, alkyl, alkoxy and alkylthio with in each case 1 to 4 carbon atoms and halogenoalkyl, halogenoalkoxy and halogenoalkylthio with in each case 1 or 2 carbon atoms and 1 to 5 identical or different halogen atoms, such as, preferably, fluorine and chlorine.
The following heterocyclic radicals may be mentioned specifically as preferred:
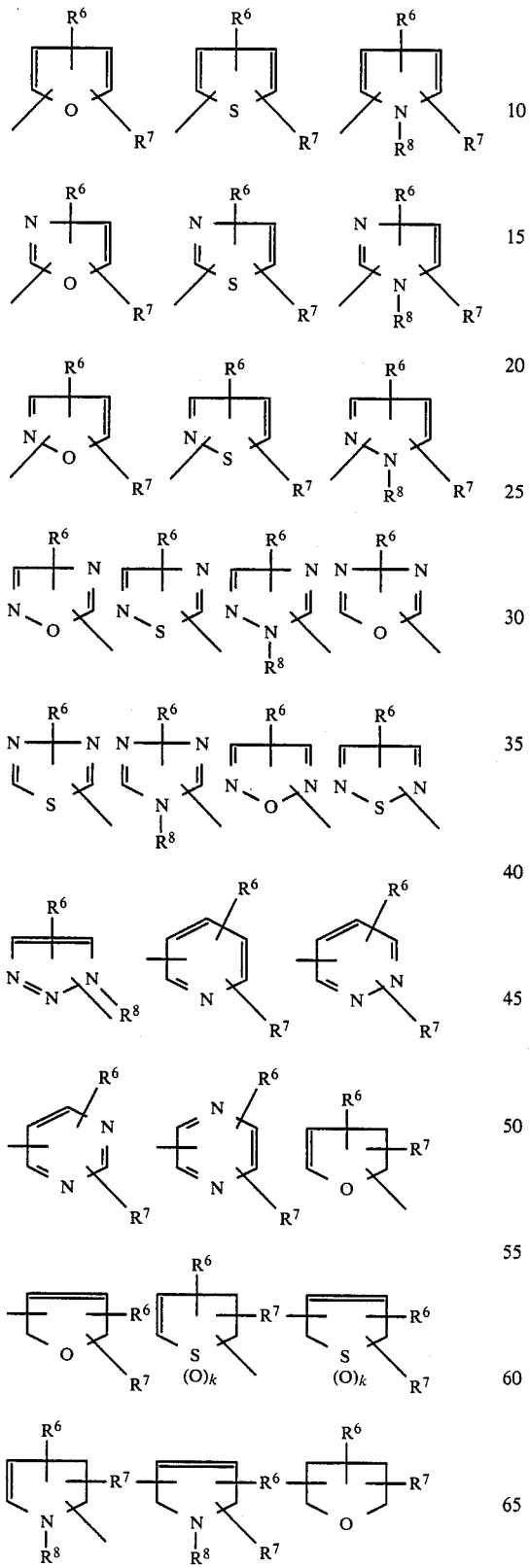
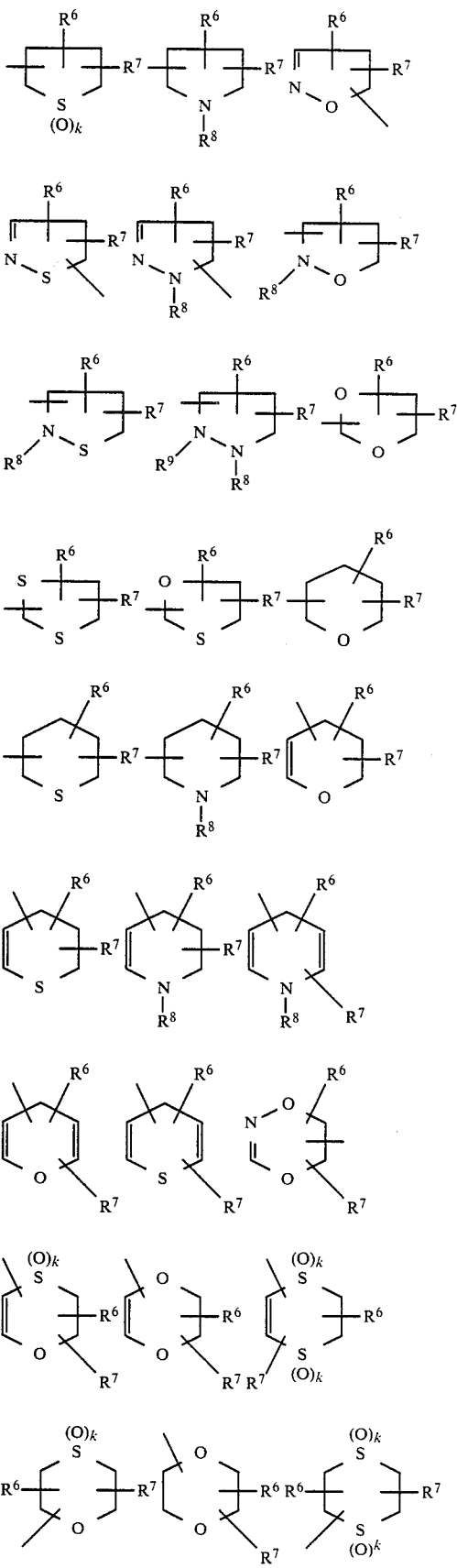

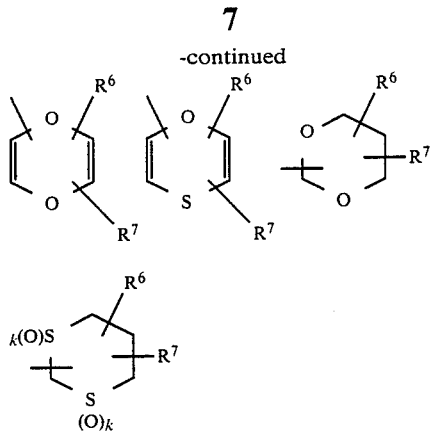

wherein, preferably, in these heterocyclic radicals,
$R^6$ and $R^7$ independently of one another represent hydrogen, halogen, alkyl, alkoxy or alkylthio with in each case 1 to 4 carbon atoms; or halogenoalkyl, halogenoalkoxy or halogenoalkylthio with in each case 1 or 2 carbon atoms and 1 to 5 identical or different halogen atoms, such as, in particular, fluorine and chlorine;
$R^8$ represents hydrogen or alkyl with 1 to 4 carbon atoms and
k represents the integer 0, 1 or 2.

Particularly preferred 5-acylamino-pyrazole derivatives of the formula (I) are those in which
$R^1$ represents hydrogen, nitro, chlorine or bromine;
$R^2$ represents hydrogen, or represents straight-chained or branched alkyl with 1 to 8 carbon atoms, or represents straight-chain or branched alkenyl or alkinyl with in each case 3 to 6 carbon atoms;
$R^3$ represents hydrogen or methyl;
$R^4$ represents hydrogen or methyl;
X represents oxygen or sulphur;
n represents the integer 0 or 1;
Ar represents phenyl which is optionally mono-, di-, tri-, tetra- or pentasubstituted by identical or different substituents, or represents 2-pyridyl, 3-pyridyl or 4-pyridyl, in each case optionally mono-, or di-, tri- or tetrasubstituted by identical or different substituents, possible substituents on the phenyl and the pyridyl being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, difluorochloromethyl, difluorochloroethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy and a radical $-S(O)_m-R^5$, wherein $R^5$ represents amino, methylamino, ethylamino, dimethylamino, diethylamino, fluorodichloromethyl, difluoromethyl, tetrafluoroethyl, trifluorochloroethyl, trichloroethyl, trichloromethyl, trifluoromethyl, methyl or ethyl and m represents the integer 0, 1 or 2, and Het represents a 5- or 6-membered unsaturated, partly saturated or saturated heterocyclic radical which has one to three identical or different hetero atoms (oxygen, nitrogen or sulphur), is optionally monosubstituted, disubstituted or trisubstituted by identical or different substituents and is linked via a carbon atom, substituents which may be mentioned being: chlorine, bromine, methyl, methoxy, methylthio and trifluoromethyl.

The following heterocyclic radicals may be mentioned specifically as particularly preferred:

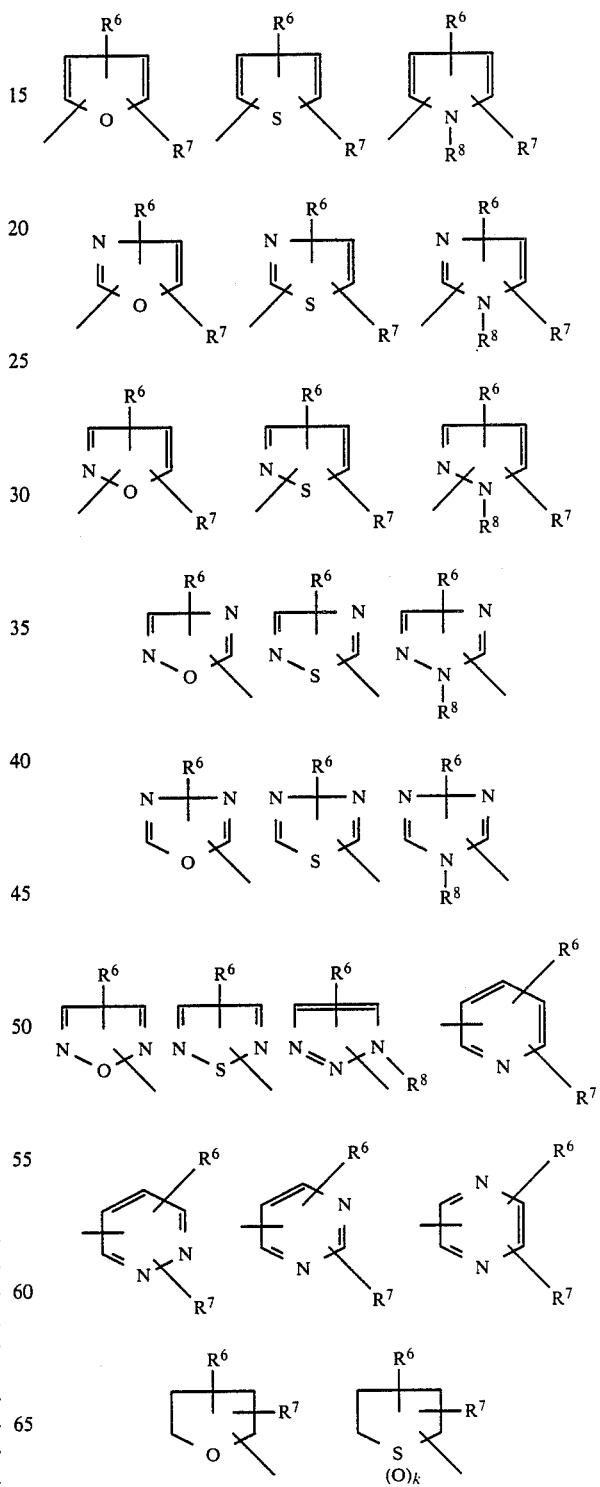

-continued

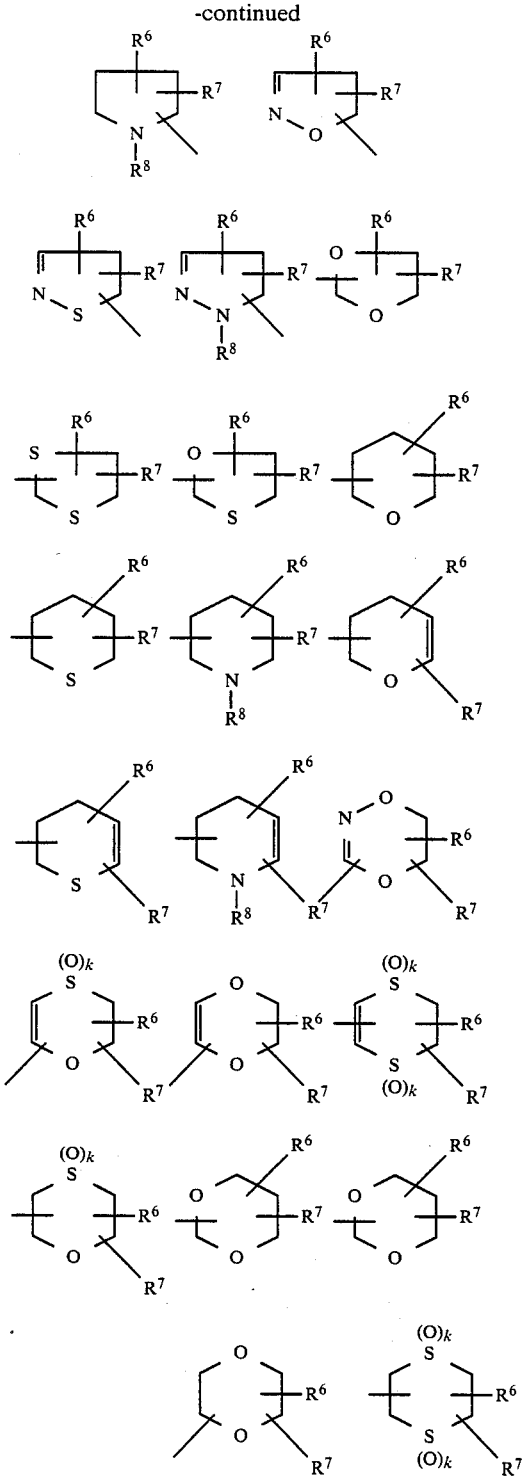

wherein, particularly preferably, in these heterocyclic radicals,

R⁶ and R⁷ independently of one another represent hydrogen, chlorine, bromine, methyl, methoxy, methylthio or trifluoromethyl;

R⁸ represents hydrogen or methyl and k represents the integer 0, 1 or 2.

Especially preferred 5-acylamino-pyrazole derivatives of the formula (I) are those in which R¹ represents hydrogen or nitro;

R² represents hydrogen, methyl, ethyl, allyl or propargyl;

R³ represents hydrogen;

R⁴ represents hydrogen;

X represents oxygen or sulphur;

n represents the integer 0 or 1;

Ar represents phenyl which is optionally mono-, di-, tri-, tetra- or pentasubstituted by identical or different substituents, or represents 2-pyridyl which is optionally mono-, di-, tri- or tetrasubstituted by identical or different substituents, possible substituents in each case being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a radical —S(O)$_m$—R⁵, wherein R⁵ represents amino, methylamino, ethylamino, dimethylamino, diethylamino, fluorodichloromethyl, difluoromethyl, tetrafluoroethyl, trichloroethyl, trichloromethyl, trifluoromethyl, methyl or ethyl and m represents the integer 0, 1 or 2, and Het represents a 5- or 6-membered unsaturated, saturated or partly saturated heterocyclic radical which has one to three identical or different hetero atoms (oxygen, nitrogen or sulphur), is optionally monosubstituted, disubstituted or trisubstituted by identical or different radicals from the group comprising methyl and chlorine and is linked via a carbon atom, the following heterocyclic radicals being mentioned specifically:

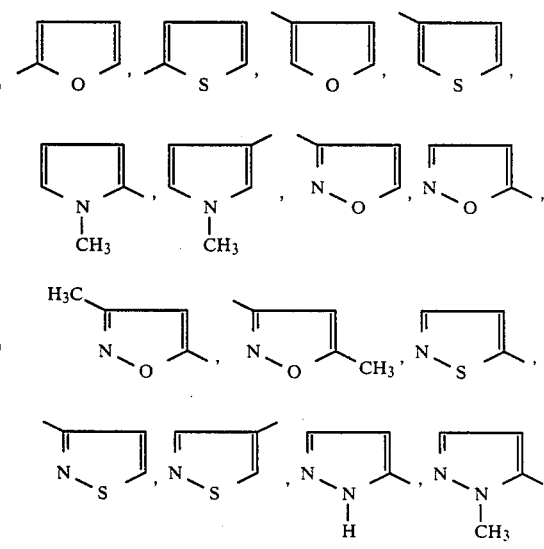

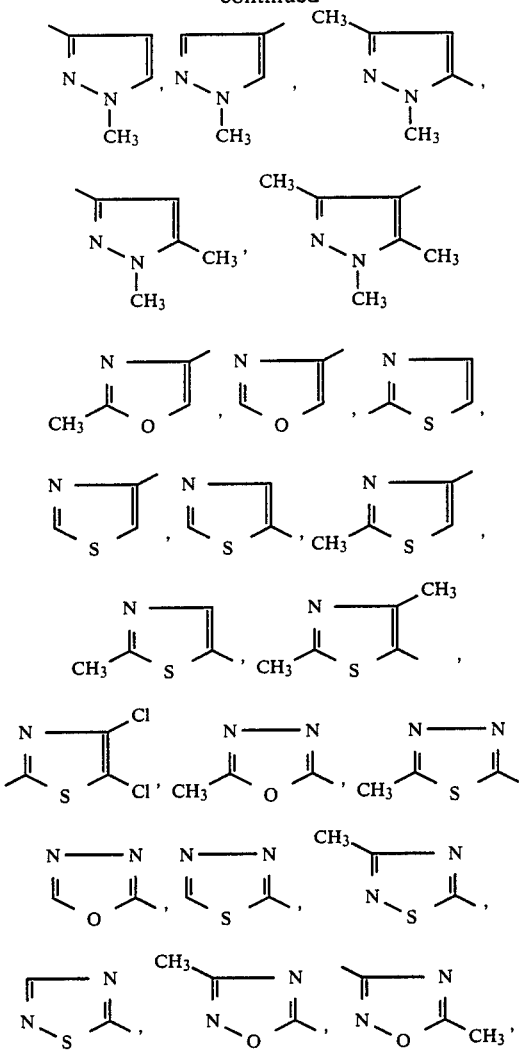
The following 5-acylamino-pyrazole derivatives of the general formula (I) may be mentioned specifically, in addition to the compounds mentioned in the preparation examples:
TABLE 1
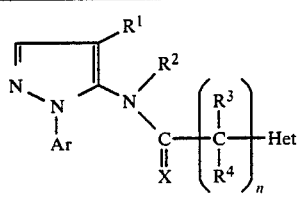
| $R^1$ | $R^2$ | $R^3$ | $R^4$ | n | X | Het | Ar |
|---|---|---|---|---|---|---|---|
| H | H | — | — | 0 | O | (furan) | (2-Cl-4-CF₃-phenyl) |
| NO₂ | H | — | — | 0 | O | (furan) | (2-Cl-4-CF₃-phenyl) |

TABLE 1-continued

Structure (I):
Pyrazole with N-Ar, R¹ at 4-position, N(R²)-C(=X)-(CR³R⁴)ₙ-Het substituent at 5-position.

| R¹ | R² | R³ | R⁴ | n | X | Het | Ar |
|---|---|---|---|---|---|---|---|
| Cl | H | — | — | 0 | O | 2-furyl | 2-Cl-4-CF₃-phenyl |
| Br | H | — | — | 0 | O | 2-furyl | 2-Cl-4-CF₃-phenyl |
| H | H | — | — | 0 | O | 2-thienyl | 2-Cl-4-CF₃-phenyl |
| NO₂ | H | — | — | 0 | O | 2-thienyl | 2-Cl-4-CF₃-phenyl |
| H | H | — | — | 0 | O | 2-pyrrolyl | 2-Cl-4-CF₃-phenyl |
| NO₂ | H | — | — | 0 | O | 2-pyrrolyl | 2-Cl-4-CF₃-phenyl |
| H | H | — | — | 0 | O | 2-furyl | 2-Cl-4-CF₃-phenyl |
| NO₂ | H | — | — | 0 | O | 2-furyl | 2-Cl-4-CF₃-phenyl |
| H | H | — | — | 0 | O | 2-tetrahydrofuryl | 2-Cl-4-CF₃-phenyl |

TABLE 1-continued

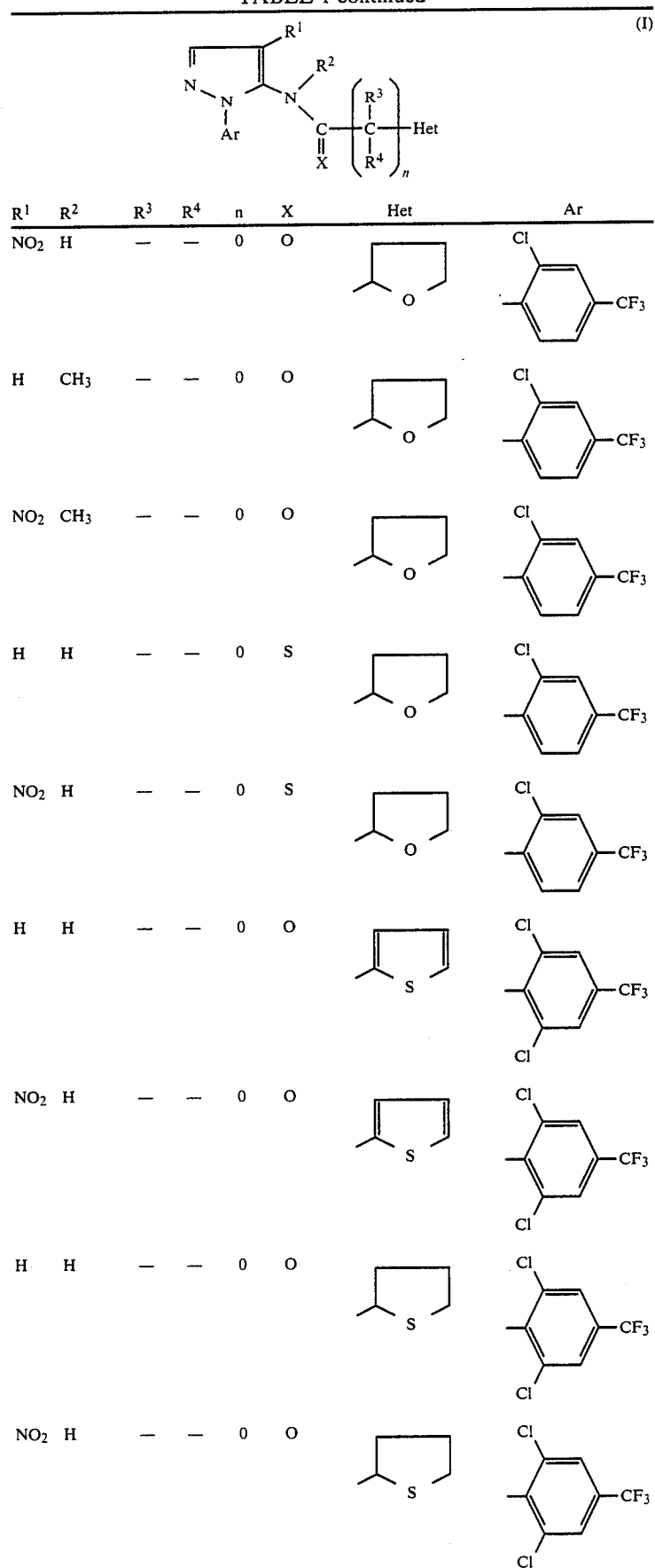

| R¹ | R² | R³ | R⁴ | n | X | Het | Ar |
|---|---|---|---|---|---|---|---|
| NO₂ | H | — | — | 0 | O | tetrahydrofuran-2-yl | 2-Cl-4-CF₃-phenyl |
| H | CH₃ | — | — | 0 | O | tetrahydrofuran-2-yl | 2-Cl-4-CF₃-phenyl |
| NO₂ | CH₃ | — | — | 0 | O | tetrahydrofuran-2-yl | 2-Cl-4-CF₃-phenyl |
| H | H | — | — | 0 | S | tetrahydrofuran-2-yl | 2-Cl-4-CF₃-phenyl |
| NO₂ | H | — | — | 0 | S | tetrahydrofuran-2-yl | 2-Cl-4-CF₃-phenyl |
| H | H | — | — | 0 | O | thien-2-yl | 2,6-diCl-4-CF₃-phenyl |
| NO₂ | H | — | — | 0 | O | thien-2-yl | 2,6-diCl-4-CF₃-phenyl |
| H | H | — | — | 0 | O | tetrahydrothien-2-yl | 2,6-diCl-4-CF₃-phenyl |
| NO₂ | H | — | — | 0 | O | tetrahydrothien-2-yl | 2,6-diCl-4-CF₃-phenyl |

TABLE 1-continued
| R¹ | R² | R³ | R⁴ | n | X | Het | Ar |
|---|---|---|---|---|---|---|---|
| H | H | — | — | 0 | S | 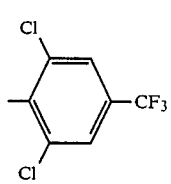 |  |
| NO₂ | H | — | — | 0 | S | 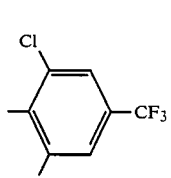 |  |
| H | H | — | — | 0 | O | 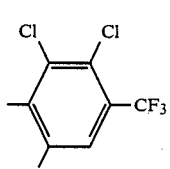 |  |
| NO₂ | H | — | — | 0 | O | 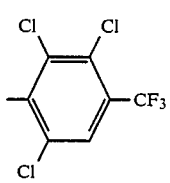 |  |
| H | H | — | — | 0 | O | 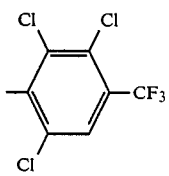 |  |
| NO₂ | H | — | — | 0 | O | 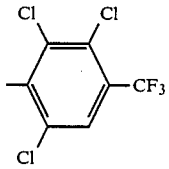 |  |
| H | H | — | — | 0 | O | 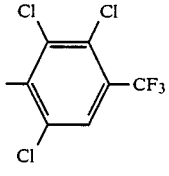 | |

TABLE 1-continued

Structure (I):

| R¹ | R² | R³ | R⁴ | n | X | Het | Ar |
|---|---|---|---|---|---|---|---|
| NO₂ | H | — | — | 0 | O | 2-thienyl (tetrahydro) | 2,3-dichloro-5-chloro-4-CF₃-phenyl |
| H | H | — | — | 0 | O | 2-furyl | pentafluorophenyl-CF₃ |
| NO₂ | H | — | — | 0 | O | 2-furyl | pentafluorophenyl-CF₃ |
| H | H | — | — | 0 | O | 2-thienyl | pentafluorophenyl-CF₃ |
| NO₂ | H | — | — | 0 | O | 2-thienyl | pentafluorophenyl-CF₃ |
| H | H | — | — | 0 | O | 2-furyl | 2-Br-4-CF₃-6-Cl-phenyl |
| NO₂ | H | — | — | 0 | O | 2-furyl | 2-Br-4-CF₃-6-Cl-phenyl |
| H | H | — | — | 0 | O | 2-furyl (tetrahydro) | 2-Br-4-CF₃-6-Cl-phenyl |

TABLE 1-continued
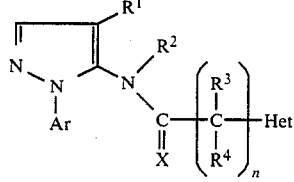
(I)
| R¹ | R² | R³ | R⁴ | n | X | Het | Ar |
|---|---|---|---|---|---|---|---|
| NO₂ | H | — | — | 0 | O | 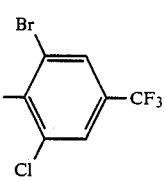 |  |
| H | H | — | — | 0 | O | 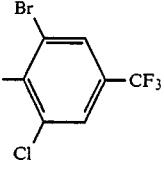 | 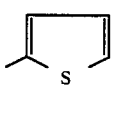 |
| NO₂ | H | — | — | 0 | O | 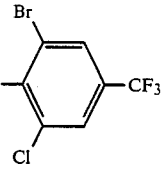 | 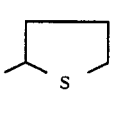 |
| H | H | — | — | 0 | O | 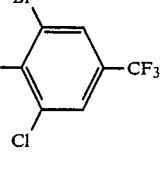 | 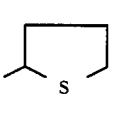 |
| NO₂ | H | — | — | 0 | O | 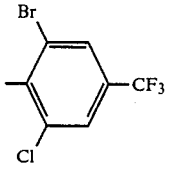 | 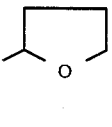 |
| H | H | — | — | 0 | O | 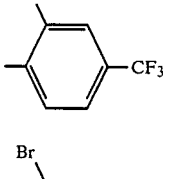 | 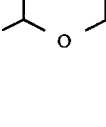 |
| NO₂ | H | — | — | 0 | O | 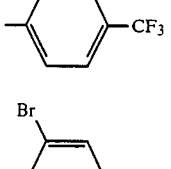 | 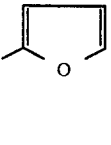 |
| H | H | — | — | 0 | O | 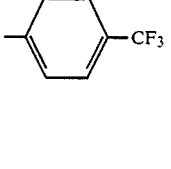 | |

TABLE 1-continued (I)

Structure: Pyrazole with Ar on N1, R¹ at C4, N(R²)-C(=X)-C(R³)(R⁴)ₙ-Het at C5.

| R¹ | R² | R³ | R⁴ | n | X | Het | Ar |
|---|---|---|---|---|---|---|---|
| NO₂ | H | — | — | 0 | O | 2-furyl | 2-bromo-4-(trifluoromethyl)phenyl |
| NO₂ | H | — | — | 0 | O | 1,3-dioxolan-2-yl | 2,5-dichloro-4-(trifluoromethyl)phenyl |
| NO₂ | H | — | — | 0 | O | 1,3-dioxolan-2-yl | 2,3,5-trichloro-4-(trifluoromethyl)phenyl |
| NO₂ | H | — | — | 0 | O | 1,3-dioxolan-2-yl | 2,3,5,6-tetrafluoro-4-(trifluoromethyl)phenyl |
| NO₂ | H | — | — | 0 | O | tetrahydropyran-2-yl | 2,5-dichloro-4-(trifluoromethyl)phenyl |
| NO₂ | H | — | — | 0 | O | tetrahydropyran-2-yl | 2,3,5-trichloro-4-(trifluoromethyl)phenyl |
| NO₂ | H | — | — | 0 | O | tetrahydropyran-2-yl | 2,3,5,6-tetrafluoro-4-(trifluoromethyl)phenyl |
| NO₂ | H | — | — | 0 | O | 3,4-dihydro-2H-pyran-2-yl | 2,5-dichloro-4-(trifluoromethyl)phenyl |

TABLE 1-continued
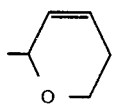
(I)
| R¹ | R² | R³ | R⁴ | n | X | Het | Ar |
|---|---|---|---|---|---|---|---|
| NO₂ | H | — | — | 0 | O | 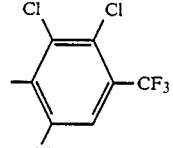 | 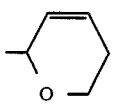 |
| NO₂ | H | — | — | 0 | O | 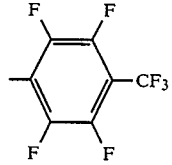 | 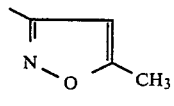 |
| NO₂ | H | — | — | 0 | O | 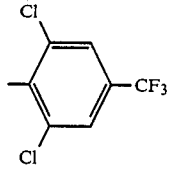 | 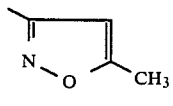 |
| NO₂ | H | — | — | 0 | O | 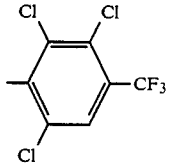 | 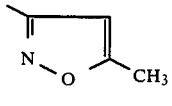 |
| NO₂ | H | — | — | 0 | O | 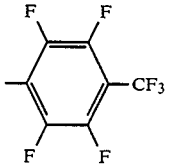 | 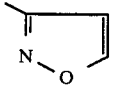 |
| NO₂ | H | — | — | 0 | O | 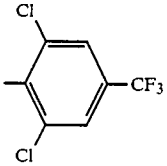 | 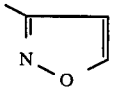 |
| NO₂ | H | — | — | 0 | O | 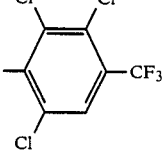 | 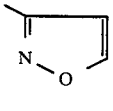 |
| NO₂ | H | — | — | 0 | O | 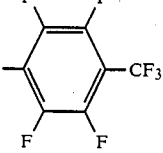 | |

TABLE 1-continued
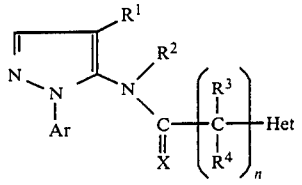
(I)
| R¹ | R² | R³ | R⁴ | n | X | Het | Ar |
|---|---|---|---|---|---|---|---|
| NO₂ | H | — | — | 0 | O | 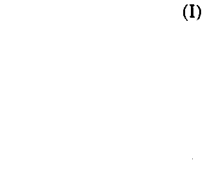 | 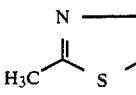 |
| NO₂ | H | — | — | 0 | O | 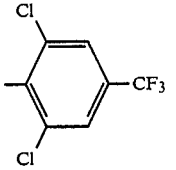 | 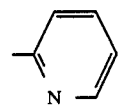 |
| NO₂ | H | — | — | 0 | O | 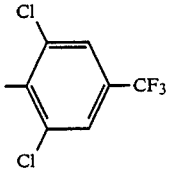 | 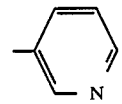 |
| NO₂ | H | — | — | 0 | O | 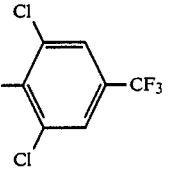 | 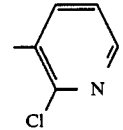 |
| NO₂ | H | — | — | 0 | O | 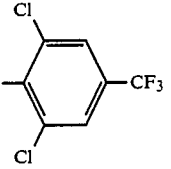 | 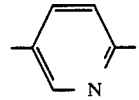 |
| NO₂ | H | — | — | 0 | O | 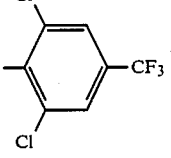 | 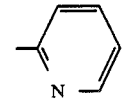 |
| NO₂ | H | — | — | 0 | O | 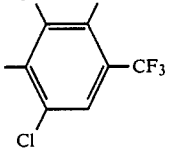 | |

TABLE 1-continued
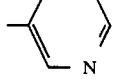
| R¹ | R² | R³ | R⁴ | n | X | Het | Ar |
|---|---|---|---|---|---|---|---|
| NO$_2$ | H | — | — | 0 | O | 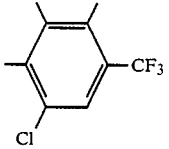 | 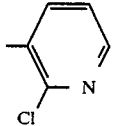 |
| NO$_2$ | H | — | — | 0 | O | 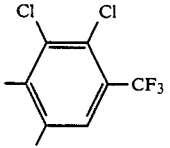 | 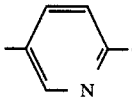 |
| NO$_2$ | H | — | — | 0 | O | 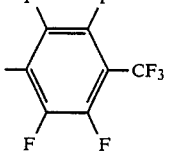 | 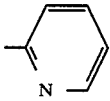 |
| NO$_2$ | H | — | — | 0 | O | 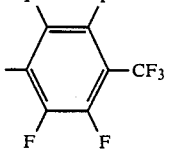 | 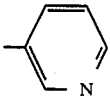 |
| NO$_2$ | H | — | — | 0 | O | 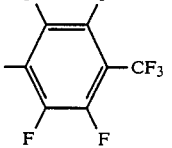 | 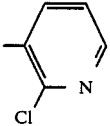 |
| NO$_2$ | H | — | — | 0 | O | 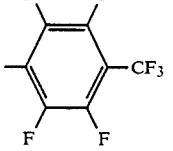 | 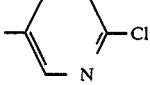 |
| NO$_2$ | H | — | — | 0 | O | 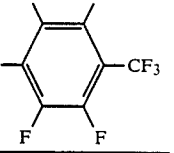 | |
If, for example, 5-amino-4-chloro-1-(2,6-dichloro-4-trifluoromethyl-phenyl)-pyrazole and furan-2-carboxylic acid chloride are used as starting substances, the course of the reaction in process (a) according to the invention can be represented by the following equation:

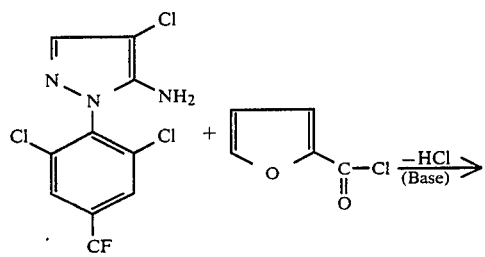

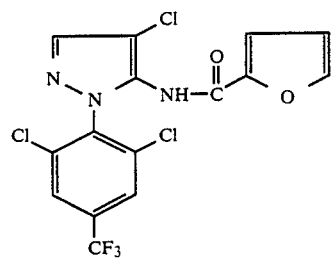

If, for example, 5-(furan-2-carboxamido)-1-(2,6-dichloro-4-trifluoromethyl-phenyl)-pyrazole and dimethyl sulphate are used as starting substances, the course of the reaction in process (b) according to the invention can be represented by the following equation:

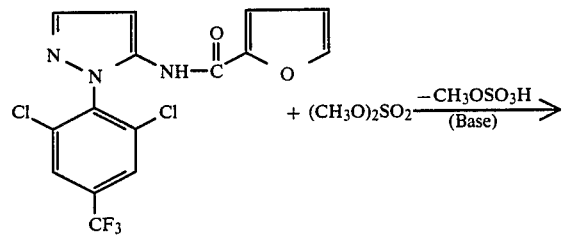

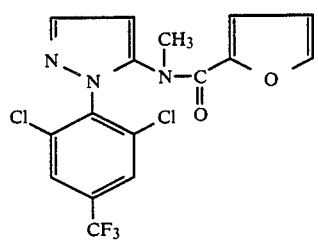

If, for example, 5-(tetrahydrofuran-2-carboxamido)-1-(2-chloro-4-trifluoromethyl-phenyl)-pyrazole and nitric acid are used as starting substances, the course of the reaction in process (c) according to the invention can be represented by the following equation:

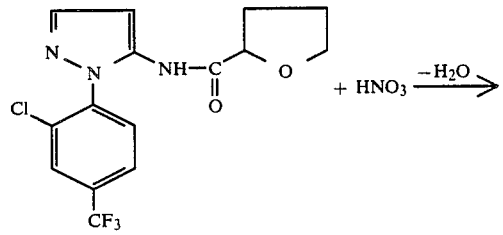

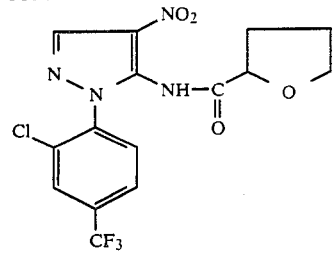

Formula (II) provides a general definition of the 5-amino-1-aryl-pyrazoles required as starting substances for carrying out process (a) according to the invention. In this formula (II), $R^1$ and Ar preferably represent those radicals which have already been mentioned as preferred for these substituents in connection with the description of the substances of the formula (I) according to the invention.

The 5-amino-1-aryl-pyrazoles of the formula (II) are known in some cases (compare, for example, U.S. Pat. No. 4,614,533, and some of them are the subject of commonly assigned Application Ser. No. 866,638, filed May 22, 1986, now pending and are obtainable analogously to known processes (compare U.S. Pat. No. 4,614,533), for example by a procedure in which arylhydrazines of the formula (VI)

in which

Ar has the abovementioned meaning, and 2-halogenoacrylonitriles of the formula (VII)

in which

Hal represents halogen, in particular chlorine or bromine, are either reacted in a 1st stage, if appropriate in the presence of a diluent, such as, for example, glacial acetic acid or ethanol, and if appropriate in the presence of a reaction auxiliary, such as, for example, sodium acetate, at temperatures between $-20°$ C. and $+20°$ C., to give the arylhydrazine derivatives of the formula (VIII)

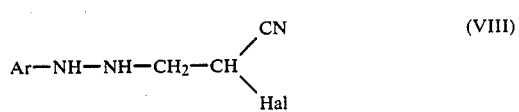

in which

Ar and Hal have the abovementioned meaning, and these are cyclized in a 2nd stage, if appropriate in the presence of a diluent, such as, for example, ethylene glycol monoethyl ether, and if appropriate in the presence of an acid catalyst, such as, for example, sulphuric acid or phosphoric acid, at temperatures between $+50°$ C. and $+150°$ C., or the compounds are cyclized directly in one reaction step, without isolation of the intermediate stage of the formula (VIII), if appropriate in the presence of a diluent, such as, for example, ethylene glycol monoethyl ether or ethanol, at temperatures between +50° C. and +150° C., and the 4-unsubstituted 5-amino-pyrazoles thus obtainable, of the formula (IIa)

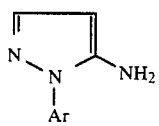

in which
Ar has the abovementioned meaning,
are nitrated in a subsequent reaction with a nitrating agent, such as, for example, nitric acid, if appropriate in the presence of a diluent, such as, for example, glacial acetic acid, and if appropriate in the presence of a reaction auxiliary, such as, for example, acetic anhydride, at temperatures between −20° C. and +50° C., or, alternatively, are halogenated with a halogenating agent, such as, for example, chlorine, sulphuryl chloride, phosphorus pentachloride, N-chlorosuccinimide, bromine, phosphorus tribromide or N-bromosuccinimide, if appropriate in the presence of a diluent, such as, for example, methylene chloride or glacial acetic acid, and if appropriate in the presence of a reaction auxiliary, such as, for example, boron trifluoride, at temperatures between −20° C. and +50° C.

It may thereby be of advantage, if appropriate, for the amino group in the 5-position of the pyrazole ring to be protected with the aid of the customary protective group techniques, for example by acylation, before the halogenation or nitration reaction and for the amino-protective group to be split off again, likewise in the customary manner, for example by hydrolysis with an aqueous or alcoholic base, when the halogenation or nitration has taken place.

The arylhydrazines (VI) are known (compare, for example, U.S. Pat. No. 4,127,575; U.S. Pat. No. 3,609,158; DE-OS (German Published Specification) No. 2,558,399; and J. Chem. Soc. C 1971, 167–174) or they can be obtained by known processes in a simple analogous manner (compare, for example, Houben-Weyl "Methoden der organischen Chemie" ("Methods of Organic Chemistry") Volume X/2, page 203, Thieme Verlag Stuttgart 1967; and U.S. Pat. No. 4,614,533).

The halogenoacrylonitriles of the formula (VII) are generally known compounds of organic chemistry.

Formula (III) provides a general definition of the acylating agents furthermore required as starting substances for carrying out process (a) according to the invention. In this formula (III), X, $R^3$, $R^4$, Het and the index n preferably represent those radicals which have already been mentioned as preferred for these substituents in connection with the description of the substances of the formula (I) according to the invention.

$E^1$ preferably represents halogen, in particular chlorine or bromine, or represents a radical

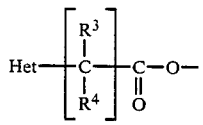

wherein
X, $R^3$, $R^4$, Het and the index n have the above-mentioned meaning.

The acylating agents of the formula (III) are generally known compounds of organic chemistry.

Formula (Ia) provides a general definition of the 5-acylamino-pyrazole derivatives required as starting substances for carrying out process (b) according to the invention. In this formula (Ia), $R^1$, X, $R^3$, $R^4$, Ar, Het and the index n preferably represent those radicals which have already been mentioned as preferred for these substituents in connection with the description of the substances of the formula (I) according to the invention.

The 5-acylamino-pyrazole derivatives of the formula (Ia) are compounds according to the invention and are obtainable with the aid of processes (a) or (c) according to the invention.

Formula (IV) provides a general definition of the alkylating agents furthermore required as starting substances for carrying out process (b) according to the invention. In this formula (IV), $R^{2-1}$ preferably represents straight-chain or branched alkyl with 1 to 12 carbon atoms, or represents straight-chain or branched alkenyl or alkinyl with in each case 3 to 8 carbon atoms, or represents cycloalkyl which has 3 to 8 carbon atoms and is optionally monosubstituted or disubstituted by identical or different substituents, substituents which may be mentioned being halogen and alkyl with 1 to 4 carbon atoms. $E^2$ preferably represents chlorine, bromine or iodine, or represents methoxysulphonyloxy or p-toluenesulphonyloxy.

The reagents of the formula (IV) are generally known compounds of organic chemistry.

Formula (Id) provides a general definition of the 5-acylamino-pyrazole derivatives required as starting substances for carrying out process (c) according to the invention. In this formula (Id), $R^2$, X, $R^3$, $R^4$, Ar, Het and the index n preferably represent those radicals which have already been mentioned as preferred for these substituents in connection with the description of the substances of the formula (I) according to the invention.

The 5-acylamino-pyrazole derivatives of the formula (Id) are compounds according to the invention and are obtainable with the aid of processes (a) or (b) according to the invention.

Formula (V) provides a general definition of the halogenating or nitrating agents furthermore required as starting substances for carrying out process (c) according to the invention. In this formula (V), $R^{1-1}$ preferably represents chlorine, bromine or nitro.

$E^3$ preferably represents a customary leaving group, such as, for example, halogen or phosphorus- or sulphur-containing halogenated leaving groups. Examples of suitable halogenating and nitrating agents are elemental chlorine or bromine, nitric acid, nitrating acid, sulphuryl chloride, phosphorus oxychloride, phosphorus oxybromide, phosphorus tribromide and similar generally customary halogenating and nitrating agents.

The halogenating and nitrating agents of the formula (V) are generally known compounds.

Possible diluents for carrying out process (a) according to the invention are inert organic solvents.

These include, in particular, aliphatic or aromatic, optionally halogenated hydrocarbons, such as, for example, benzine, benzene, toluene, xylene, chlorobenzene, petroleum ether, hexane, cyclohexane, methylene chloride, chloroform and carbon tetrachloride, ethers, such as diethyl ether, dioxane, tetrahydrofuran or ethylene glycol dimethyl or diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric acid triamide, esters, such as ethyl acetate, or sulphoxides, such as dimethylsulphoxide.

If appropriate, the process according to the invention is carried out in the presence of a suitable acid-binding agent.

Possible acid-binding agents are all the customary inorganic or organic bases. These include, for example, alkali metal hydroxides, such as sodium hydroxide or potassium hydroxide, alkali metal carbonates, such as sodium carbonate, potassium carbonate or sodium bicarbonate, and tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

If appropriate, process (a) according to the invention can also be carried out in the presence of a suitable acylation catalyst. Acylation catalysts which are preferably used are proton acids, such as sulphuric acid, hydrochloric acid, phosphoric acid or trifluoroacetic acid, or Lewis acids, such as aluminum trichloride, boron trifluoride or iron trichloride.

The reaction temperatures can be varied within a substantial range in carrying out process (a) according to the invention. The reaction is in general carried out at temperatures between $-20°$ C. and $+150°$ C., preferably at temperatures between 0° C. and 100° C.

For carrying out process (a) according to the invention, in general 1.0 to 15.0 mols, preferably 1.0 to 5.0 mols, of acylating agent of the formula (III) and if appropriate 1.0 to 3.0 mols, preferably 1.0 to 2.0 mols, of acid-binding agent or if appropriate 0.1 to 3.0 mols, preferably 0.1 to 2.0 mols, of acylation catalyst are employed per mol of 5-amino-1-aryl-pyrazole of the formula (II). The reaction is carried out and the reaction products of the formula (Ia) are worked up and isolated by customary known methods.

Possible diluents for carrying out process (b) according to the invention are likewise inert organic solvents. The organic solvents mentioned for process (a) are preferably used.

If appropriate, process (b) according to the invention can also be carried out in a two-phase system, such as, for example, water/toluene or water/methylene chloride, and if appropriate in the presence of a phase transfer catalyst. Examples of such catalysts which may be mentioned are: tetrabutylammonium iodide, tetrabutylammonium bromide, tributyl-methylphosphonium bromide, trimethyl-$C_{13}$/$C_{15}$-alkylammonium chloride, dimethyl-dibenzylammonium methyl-sulphate, dimethyl-$C_{12}$/$C_{14}$-alkyl-benzylammonium chloride, tetrabutylammonium hydroxide, 15-crown-5,18-crown-6, triethylbenzylammonium chloride and trimethylbenzylammonium chloride.

Possible acid-binding agents for carrying out preparation process (b) are all the inorganic and organic bases which can usually be employed. Bases which are preferably used are alkali metal hydrides, hydroxides, amides, carbonates or bicarbonates, such as, for example, sodium hydride, sodium amide, sodium hydroxide, sodium carbonate or sodium bicarbonate, or tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU).

The reaction temperatures can be varied within a substantial range in carrying out process (b) according to the invention. The reaction is in general carried out at temperatures between $-20°$ C. and $+150°$ C., preferably at temperatures between 0° C. and $+100°$ C.

For carrying out process (b) according to the invention, in general 1.0 to 20.0 mols, preferably 1.0 to 15.0 mols, of alkylating agent of the formula (IV) and if appropriate 1.0 to 3.0 mol, preferably 1.0 to 2.0 mols, of acid-binding agent and if appropriate 0.01 to 1.0 mols of phase transfer catalyst are employed per mol of 5-acylamino-pyrazole derivatives of the formula (Ia). The reaction is carried out and the reaction products of the formula (Ib) are worked up and isolated in the generally customary manner.

Possible diluents for carrying out preparation process (c) are all the solvents which can usually be employed for such electrophilic substitution reactions. The acids or mixtures which can be used as reagents, such as, for example, nitric acid, sulphuryl chloride or nitrating acid, are preferably used simultaneously as the diluent. If appropriate, inert organic solvents, such as, for example, glacial acetic acid or chlorinated hydrocarbons, such as methylene chloride, chloroform or carbon tetrachloride, can also be used as diluent.

Possible catalysts or reaction auxiliaries for carrying out preparation process (c) are likewise the catalysts which are customary for such reactions; acid catalysts, such as, for example, sulphuric acid, iron-III chloride or other Lewis acids or acetic anhydride, are preferably used.

The reaction temperatures can be varied within a substantial range in carrying out preparation process (c). The reaction is in general carried out between $-50°$ C. and $+200°$ C., preferably between $-20°$ C. and $+150°$ C.

For carrying out preparation process (c), in general 1.0 to 10.0 mols, preferably 1.0 to 5.0 mols, of halogenating or nitrating agent of the formula (V) and if appropriate 0.1 to 10 mols, preferably 1.0 to 5.0 mols, of catalyst or reaction auxiliary are employed per mol of 5-acylamino-pyrazole derivative of the formula (Id). The reaction is carried out and the reaction products of the formula (Ic) are worked up and isolated in the generally customary manner.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can thereby be used with particularly good success for selectively combating monocotyledon and dicotyledon weeds, in mono- and dicotyledon crops, such as, for example, soy beans, barley, wheat or corn.

The intermediate products of the formula (II) also have a good herbicidal activity.

The active compounds according to the invention also engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular desired manner.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The active compounds can be converted to the customary formulations, such as solutions, emulsions, suspensions, powders, foams, pastes, granules, aerosols, very fine capsules in polymeric substances and in coating compositions for use on seed, as well as ULV formulations.

These formulations are produced in known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide.

As solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian blue, and organic dyestuffs, such as alizarin dyestuffs, azo dyestuffs and metal phthalocyanine dyestuffs, and trace nutrients such as salts or iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 4-amino-6-t-butyl-3-ethylthio-1,2,4-triazin-5(4H)-one or N-(2-benzothiazolyl)N,N'-dimethyl-urea, for combating weeds in cereals; 4-amino-3-methyl-6-phenyl-1,2,4-triazin-5(4H)-one for combating weeds in sugar beet and 4-amino-6-(1,1-dimethylethyl)-3-methylthio-1,2,4-triazin-5(4H)-one for combating weeds in soy beans.

Mixtures with N,N-dimethyl-N'-(3-chloro-4-methylphenyl)-urea; N,N-dimethyl-N'-(4-isopropylphenyl)- urea; 1-amino-6-ethylthio-3-(2,2-dimethylpropyl)-1,3,5-triazine-2,4(1H,3H)-dione; 2,4-dichlorophenoxyacetic acid; 2,4-dichlorophenoxypropionic acid; (2-methyl-4-chlorophenoxy)acetic acid; (4-chloro-2-methylphenoxy)-propionic acid; chloroacetic acid N-(methoxymethyl)-2,6-diethylanilide; 2-ethyl-6-methyl-N-(1-methyl-2-methoxyethyl)-chloracetanilide; 2,6-dinitro-4-trifluoromethyl-N,N-dipropylaniline; 2-benzyloxyethyl, trimethylsilylmethyl or 2,2-diethoxyethyl 2-[4-(3,5-dichloropyrid-2-yloxy)-phenoxy]propionate; 3,5-diiodo-4-hydroxybenzonitrile); 3-isopropyl-2,1,3-benzothiadiazin-4-one 2,2-dioxide; 2-chloro-N-{[(4-methoxy-6-methyl-1,3,5-triazin-2-yl)-amino]-carbonyl}-benzenesulphonamide; N-(1-ethylpropyl)-3,4-dimethyl-2,6-dinitroaniline; O-(6-chloro-3-phenyl-pyridazin-4-yl) S-octyl thiocarbonate; S-(2,3,3-trichloroallyl) N,N-diisopropyl-thiolcarbamate; N-methyl-2-(1,3-benzothiazol-2-yloxy)-acetanilide; exo-1-methyl-4-(1-methylethyl)-2-(2-methylphenyl-methoxy)-7-oxabicyclo-(2,2,1)-heptane; 2-{4-[(3-chloro-5-(trifluoromethyl)-2-pyridinyl)-oxy]-phenoxy}-propionic acid and -propanoic acid ethyl ester; 3,5-di-bromo-4-hydroxy-benzonitrile; 2-[5-methyl-5-(1-methyl-ethyl)-4-oxo-2-imidazolin-2-yl]-3-quinolinecarboxylic acid or 1-(3-trifluoromethyl-phenyl)-4-methylamino-5-chloropyridaz-6-one, if appropriate, are also of advantage.

Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

When the active compounds are used as plants growth regulators, the amounts applied can likewise be varied within a substantial range. In general, 0.01 to 50 kg, preferably 0.05 to 10 kg, of active compound are used per hectare of soil surface.

As regards the time of application, the growth regulators are applied within a preferred period of time, the exact definition of which depends on the climatic and vegetative circumstances.

The preparation and the use of the active compounds according to the invention can be seen from the following examples.

PREPARATION EXAMPLES

EXAMPLE 1

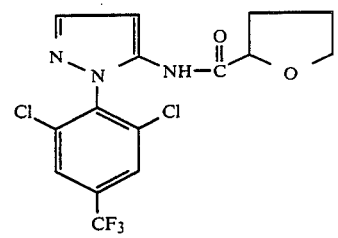

(Process a)

19.8 g (0.07 mol) of 5-amino-1-(2,6-dichloro-4-trifluoromethylphenyl)-pyrazole and 7.1 g (0.09 mol) of pyridine are dissolved in 150 ml of acetonitrile, and 12.1 g (0.09 mol) of tetrahydrofuran-2-carboxylic acid chloride are added at 25°–30° C., with stirring. The mixture is stirred at room temperature for a further 24 hours. The reaction batch is then poured onto water and extracted with chloroform; the chloroform phase is washed with aqueous sodium bicarbonate solution, dried over sodium sulphate and concentrated. The oily residue is crystallized by trituration with petroleum ether. 24 g (87% of theory) of 1-(2,6-dichloro-4-trifluoromethylphenyl)-5-(2-tetrahydrofuroyl)-aminopyrazole of melting point 95°–97° C. are obtained.

Preparation of the starting substance

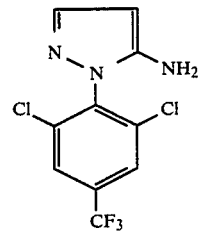

25 ml (27.6 g/0.3 mol) of 2-chloro-acrylonitrile are added dropwise to 24.5 g (0.1 mol) of 2,6-dichloro-4-trifluoromethylphenylhydrazine and 20 mg of disodium ethylenediamine-tetraacetate (Titriplex III) in 150 ml of methanol at the reflux temperature. When the addition has ended, the mixture is heated at the reflux temperature for a further 8 hours, 9 ml (0.16 mol) of 96% strength sulphuric acid are added dropwise and the mixture is heated at the reflux temperature for a further 6 hours. 33.5 g (0.3 mol) of anhydrous sodium carbonate are added to the cooled reaction mixture. After 4 hours, the solvent is removed in vacuo, the residue is taken up in 500 ml of water and the mixture is stirred at room temperature for 10 hours. The precipitate which has separated out is filtered off, rinsed with water and dried in vacuo at 50° C. 28.5 (96% of theory) of 5-amino-1-(2,6-dichloro-4-trifluoromethylphenyl)-pyrazole of melting point 103°–105° C. are obtained.

EXAMPLE 2

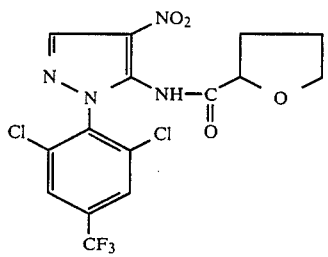

(Process c)

10.6 g (0.027 mol) of 1-(2,6-dichloro-4-trifluoromethylphenyl)-5-(2-tetrahydrofuroyl)-amino-pyrazole (Example 1) and 3 ml of acetic anhydride are dissolved in 50 ml of glacial acetic acid, and 2.2 ml of concentrated nitric acid are added at 10° C., with cooling. The mixture is then stirred at room temperature for a further 24 hours, poured into water and extracted with methylene chloride and the methylene chloride phase is then washed again with aqueous sodium bicarbonate solution, dried over sodium sulphate and concentrated.

11 g (93% of theory) of 1-(2,6-dichloro-4-trifluoromethylphenyl)-4-nitro-5-(2-tetrahydrofuroyl-)aminopyrazole of melting point 169°–172° C. are obtained.

EXAMPLE 3

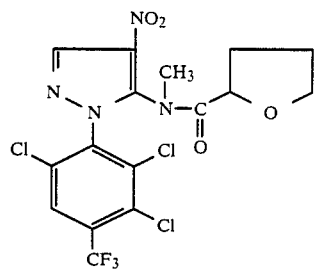

(Process b)

5.2 g (0.011 mol) of 1-(2,3,6-trichloro-4-trifluoromethyl-phenyl)-4-nitro-5-(2-tetrahydrofuroyl)-aminopyrazole are dissolved in 40 ml of acetonitrile and, after addition of 1.8 g (0.0132 mol) of powdered potassium carbonate, 1.7 g (0.0132 mol) of dimethyl sulphate are added dropwise at about 50° C. The reaction mixture is subsequently stirred at 50° to 60° C. for about a further 8 hours and is then filtered and freed from the solvent in vacuo. The residue is taken up in methylene chloride and washed several times with water and the organic phase is then dried over sodium sulphate and concentrated. 5 g of an oil remain and are chromatographed over silica gel (mobile phase: petroleum ether/ethyl acetate 8:2). The main fraction crystallizes by trituration with diisopropyl ether.

2.2 g (41% of theory) of 1-(2,3,6-trichloro-4-trifluoromethyl-phenyl)-4-nitro-5-(N-methyl-N-tetrahydrofuro-2-yl)-amino-pyrazole of melting point 142° to 143° C. are obtained.

The compounds of the formula (I) listed in the following Table 2 are obtained in accordance with the preparation examples and the general statements on the preparation:

TABLE 2

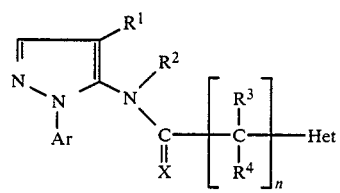

| Example No. | $R^1$ | $R^2$ | n | $R^3$ | $R^4$ | X | Het | Ar | Melting point (°C.) |
|---|---|---|---|---|---|---|---|---|---|
| 4 | H | H | 0 | — | — | O | 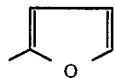 | 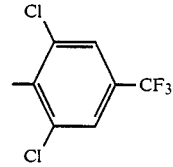 | 157–162 |
| 5 | NO$_2$ | H | 0 | — | — | O | 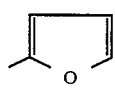 | 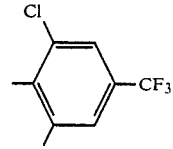 | 154–158 |

TABLE 2-continued (I)

Structure (I): pyrazole with R¹ at 4-position, N-Ar at 1-position, connected via N(R²)-C(=X)-[C(R³)(R⁴)]ₙ-Het

| Example No. | R¹ | R² | n | R³ | R⁴ | X | Het | Ar | Melting point (°C.) |
|---|---|---|---|---|---|---|---|---|---|
| 6 | H | H | 0 | — | — | O | tetrahydrofuran-2-yl | 2-Cl, 4-CF₃-phenyl | 67–71 |
| 7 | NO₂ | H | 0 | — | — | O | tetrahydrofuran-2-yl | 2-Cl, 4-CF₃-phenyl | 98–102 |
| 8 | H | H | 0 | — | — | O | tetrahydrofuran-2-yl | 2,6-diCl, 4-SO₂CF₃-phenyl | 145–151 |
| 9 | NO₂ | H | 0 | — | — | O | tetrahydrofuran-2-yl | 2,6-diCl, 4-SO₂CF₃-phenyl | 138–140 |
| 10 | H | H | 0 | — | — | O | tetrahydrofuran-2-yl | 2,6-diCl, 4-OCF₃-phenyl | 67–71 |
| 11 | NO₂ | H | 0 | — | — | O | tetrahydrofuran-2-yl | 2,6-diCl, 4-OCF₃-phenyl | 129–131 |
| 12 | H | H | 0 | — | — | O | tetrahydrofuran-2-yl | 2,3,5,6-tetraF, 4-CF₃-phenyl | oil |
| 13 | NO₂ | H | 0 | — | — | O | tetrahydrofuran-2-yl | 2,3,5,6-tetraF, 4-CF₃-phenyl | 69–71 |

TABLE 2-continued

Structure (I):
Pyrazole ring with N-N, Ar on N, R¹ at 4-position, N(R²)-C(=X)-[CR³R⁴]ₙ-Het group at 5-position.

| Example No. | R¹ | R² | n | R³ | R⁴ | X | Het | Ar | Melting point (°C.) |
|---|---|---|---|---|---|---|---|---|---|
| 14 | H | H | 0 | — | — | O | 2-tetrahydrofuryl | 2,6-dichloro-3,5-difluoro-4-CF₃-phenyl | oil |
| 15 | NO₂ | H | 0 | — | — | O | 2-tetrahydrofuryl | 2,6-dichloro-3,5-difluoro-4-CF₃-phenyl | 119–121 |
| 16 | H | H | 0 | — | — | O | 2-tetrahydrofuryl | 2,3,5-trichloro-4-CF₃-phenyl (2,6-dichloro) | oil |
| 17 | NO₂ | H | 0 | — | — | O | 2-tetrahydrofuryl | 2,6-dichloro-4-CF₃-phenyl (with extra Cl) | 129 |
| 18 | H | H | 0 | — | — | O | 2-tetrahydrofuryl | 2,6-dichloro-4-SCF₃-phenyl | 90 |
| 19 | NO₂ | H | 0 | — | — | O | 2-tetrahydrofuryl | 2,6-dichloro-4-SCF₃-phenyl | 95 |
| 20 | H | H | 0 | — | — | O | 2-methyl-1,4-oxathiine (CH₃-C=C-S-CH₂-CH₂-O-) | 2,6-dichloro-4-CF₃-phenyl | 148–56 |
| 21 | NO₂ | H | 0 | — | — | O | 3-dihydrofuryl | 2,6-dichloro-4-CF₃-phenyl | — |

TABLE 2-continued (I)

Structure: Pyrazole with R¹ at 4-position, N-Ar at 1-position, N(R²)-C(=X)-[CR³R⁴]ₙ-Het at 5-position

| Example No. | R¹ | R² | n | R³ | R⁴ | X | Het | Ar | Melting point (°C.) |
|---|---|---|---|---|---|---|---|---|---|
| 22 | H | H | 0 | — | — | O | 3-tetrahydrofuryl | 2,6-dichloro-4-(trifluoromethyl)phenyl | 183–85 |
| 23 | H | H | 0 | — | — | O | 3-tetrahydrofuryl | 2,3,5-trichloro-4-(trifluoromethyl)phenyl | 170–73 |
| 24 | H | H | 0 | — | — | O | 2-thienyl | 2,6-dichloro-4-(trifluoromethyl)phenyl | 184–86 |
| 25 | H | H | 0 | — | — | O | 5-methylisoxazol-3-yl | 2,6-dichloro-4-(trifluoromethyl)phenyl | 145–48 |
| 26 | H | H | 0 | — | — | O | 5-methylisoxazol-3-yl | 2,3,5-trichloro-4-(trifluoromethyl)phenyl | 85–86 |
| 27 | H | H | 0 | — | — | O | 2-thienyl | 2,3,5-trichloro-4-(trifluoromethyl)phenyl | 186–89 |
| 28 | NO₂ | H | 0 | — | — | O | 3-tetrahydrofuryl | 2,6-dichloro-4-(trifluoromethyl)phenyl | 168–71 |

TABLE 2-continued (I) Structure: Pyrazole with R¹, R², Ar, and C(=X)–[CR³R⁴]ₙ–Het substituents

| Example No. | R¹ | R² | n | R³ | R⁴ | X | Het | Ar | Melting point (°C.) |
|---|---|---|---|---|---|---|---|---|---|
| 29 | NO₂ | H | 0 | — | — | O | 2,3-dihydrofuran-3-yl | 2,6-dichloro-4-(trifluoromethyl)phenyl (Cl, Cl, CF₃) | 135–40 |
| 30 | NO₂ | H | 0 | — | — | O | 5-methylisoxazol-3-yl | 2,6-dichloro-4-(trifluoromethyl)phenyl | 211–14 |
| 31 | H | H | 0 | — | — | O | furan-3-yl | 2,6-dichloro-4-(trifluoromethyl)phenyl | 223–25 |
| 32 | H | H | 0 | — | — | O | furan-3-yl | 2,6-dichloro-4-(trifluoromethyl)phenyl | 206–08 |
| 33 | NO₂ | H | 0 | — | — | O | thiophen-2-yl | 2,6-dichloro-4-(trifluoromethyl)phenyl | 190–94 |
| 34 | NO₂ | H | 0 | — | — | O | 5-methylisoxazol-3-yl | 2,6-dichloro-4-(trifluoromethyl)phenyl | 149–52 |
| 35 | NO₂ | H | 0 | — | — | O | thiophen-2-yl | 2,6-dichloro-4-(trifluoromethyl)phenyl | 179–82 |
| 36 | NO₂ | H | 0 | — | — | O | furan-3-yl | 2,6-dichloro-4-(trifluoromethyl)phenyl | — |

TABLE 2-continued $$\underset{Ar}{\underset{N}{N}}\underset{N}{\overset{R^1}{\underset{\underset{X}{\parallel}}{C}}}\underset{N}{\overset{R^2}{\underset{}{N}}}\left[\underset{R^4}{\overset{R^3}{\underset{|}{C}}}\right]_n Het \qquad (I)$$

| Example No. | R¹ | R² | n | R³ | R⁴ | X | Het | Ar | Melting point (°C.) |
|---|---|---|---|---|---|---|---|---|---|
| 37 | NO₂ | H | 0 | — | — | O | tetrahydrofuran-2-yl | 2,4-dichloro-3-fluoro-5-CF₃-phenyl... (2-Cl, 4-Cl, 5-CF₃, 3-F) | 137 |
| 38 | NO₂ | H | 0 | — | — | S | tetrahydrofuran-2-yl | 2,4-dichloro-5-CF₃-phenyl | 137 |
| 39 | H | H | 0 | — | — | O | tetrahydrofuran-2-yl | 3,5-dichloropyridin-2-yl | 88 |
| 40 | NO₂ | H | 0 | — | — | O | tetrahydrofuran-2-yl | 3,5-dichloropyridin-2-yl | 56 |

USE EXAMPLES

The compound shown below was employed as the comparison substance in the use examples which follow:

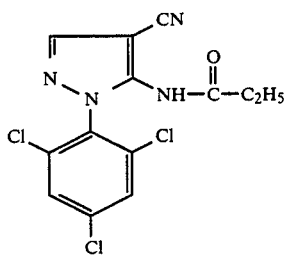

(A)

4-Cyano-5-propionamido-1-(2,4,6-trichlorophenyl)-pyrazole (known from DE-OS (German Published Specification) No. 3,226,513).

EXAMPLE A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clearly superior activity and crop plant selectivity compared with comparison substance (A) is shown, for example, by the compounds according to preparation Examples 2, 5, 13, 15, 17 and 19.

EXAMPLE B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

In this test, a clearly superior activity and crop plant selectivity compared with comparison substance (A) is shown, for example, by the compounds according to preparation Examples 2, 5, 7, 9, 11, 13, 15, 17 and 19.

EXAMPLE C

Defoliation and desiccation of the leaves of cotton
Solvent: 30 parts by weight of dimethylformamide
Emulsifier: 1 part by weight of polyoxyethylene sorbitane monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 1 week, the shedding of leaves and the desiccation of the leaves are rated, in comparison with the control plants.

In this test, for example, the active compounds according to preparation Examples 2, 5, 7, 9, 13, 15, 17, 21, 28, 29, 34, 36 and 38 show a good action.

It is understood that the specification and examples are illustrative but not limitative of the present invention and that other embodiments within the spirit and scope of the invention will suggest themselves to those skilled in the art.

We claim:

1. A 5-acylaminopyrazole derivative of the formula:

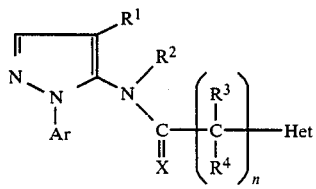

in which
R$^1$ represents hydrogen, nitro, fluorine, chlorine, bromine or iodine;
R$^2$ represents hydrogen, or represents straight-chain or branched alkyl with 1 to 12 carbon atoms, or represents straight-chain or branched alkenyl or alkinyl with in each case 3 to 8 carbon atoms, or represents cycloalkyl which has 3 to 8 carbon atoms and is optionally monosubstituted or disubstituted by halogen and/or alkyl with 1 to 4 carbon atoms;
R$^3$ represents hydrogen, or represents straight-chain or branched alkyl with 1 to 6 carbon atoms;
R$^4$ represents hydrogen, or represents straight-chain or branched alkyl with 1 to 6 carbon atoms;
X represents oxygen or sulfur;
R$^1$ represents hydrogen, nitro, chlorine or bromine;
R$_2$ represents hydrogen, or represents straight-chain or branched alkyl with 1 to 8 carbon atoms, or represents straight-chain or branched alkenyl or alkinyl with in each case 3 to 6 carbon atoms;
R$^3$ represents hydrogen or methyl;
R4 represents hydrogen or methyl;
X represents oxygen or sulfur;
n represents the integer 0 or 1;
Ar represents phenyl which is optionally mono-, di-, tri-, tetra- or pentasubstituted, or represents pyridyl optionally mono-, di-, tri- or tetrasubstituted, substituents on the phenyl or pyridyl being cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, difluorochloromethyl, difluorochloroethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy,
n represents the integer 0, 1 or 2;
Ar represents phenyl or pyridyl which are optionally substituted by cyano, nitro, halogen, alkyl, alkoxy, alkoxycarbonyl, halogenoalkyl or halogenoalkoxy wherein each alkyl moiety has 1 to 4 carbon atoms or the radical —S(O)m—R$^5$, wherein
R$^5$ represents amino or alkyl, alkylamino, dialkylamino or halogenoalkyl wherein each alkyl moiety has 1 to 4 carbon atoms and
m represents the integer 0, 1 or 2; and
Het represents a 5- or 6-membered heterocyclic radical (1) in which the component ring hetero atoms are one to three hetero atoms chosen independently from the group consisting of oxygen, sulfur, and nitrogen atoms, (2) which is linked to the depicted pyrazole ring via a carbon atom, (3) which is monosubstituted, disubstituted or trisubstituted by halogen, alkyl, alkoxy or alkylthio with in each case 1 to 4 carbon atoms, or halogenoalkyl, halogenoalkoxy or halogenoalkylthio with in each case 1 to 2 carbon atoms, and (4) in which any ring sulfur atom may optionally be doubly bound to one or two extracyclic oxygen atoms.

2. A 5-acylaminopyrazole derivative according to claim 1, difluorodichloroethoxy, trifluorodichloromethoxy, pentachloroethoxy, or the radical —S(O)m—R5, wherein
R$^5$ represents amino, methylamino, ethylamino, dimethylamino, diethylamino, fluorodichloromethyl, difluoromethyl, tetrafluoroethyl, trifluorochloroethyl, trichloroethyl, trichloromethyl, trifluoromethyl, methyl or ethyl and
m represents the integer 0, 1 or 2, and
Het represents a 5- or 6-membered heterocyclic radical (1) in which the one to three component ring heteroatoms are independently chosen from the group consisting of oxygen, nitrogen, or sulfur hetero atoms, (2) which is linked via a carbon atom, (3) which is optionally monosubstituted, disubstituted or trisubstituted by chlorine, bromine, methyl, methoxy, methylthio or trifluoromethyl and (4) in which any ring sulfur atom may optionally be doubly bound to one or two extracyclic oxygen atoms.

3. A 5-acylamino-pyrazole derivative according to claim 1, in which

Het represents

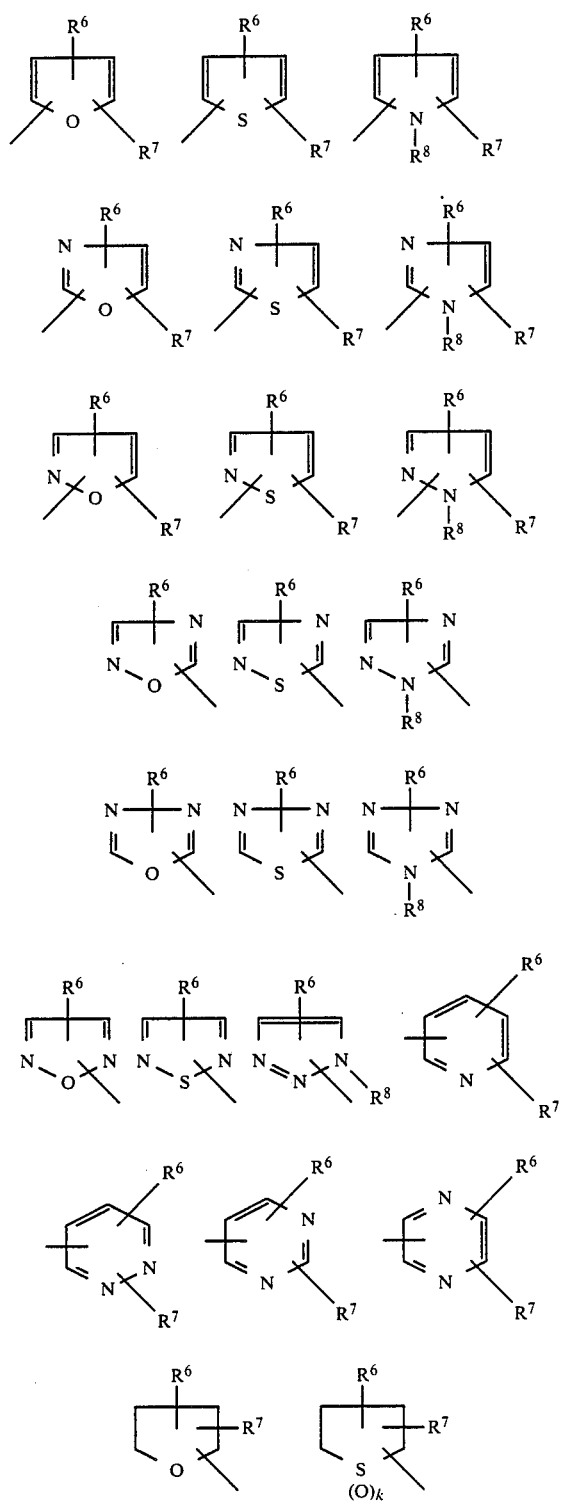

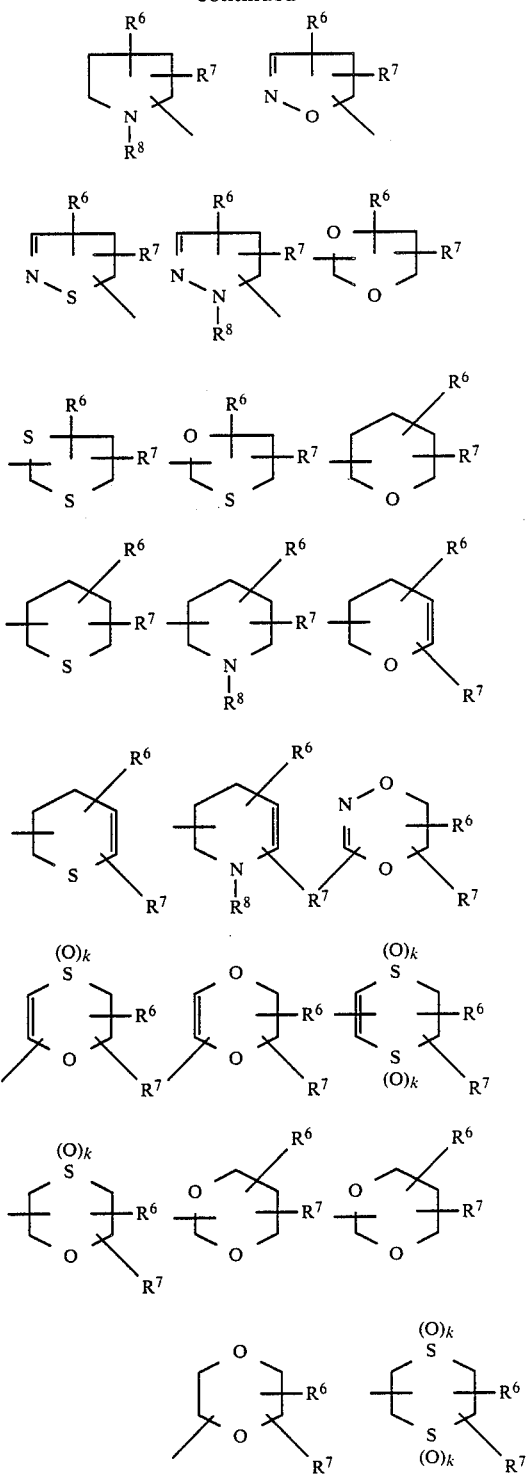

$R^6$ and $R^7$ independently of one another represent hydrogen, chlorine, bromine, methyl, methoxy methylthio or trifluoromethyl;

$R^8$ represents hydrogen or methyl and k represents the integer 0, 1 or 2.

4. A 5-acylamino-pyrazole derivative according to claim 1, in which $R^1$ represents hydrogen or nitro;

$R^2$ represents hydrogen, methyl, ethyl, allyl or propargyl;

$R^3$ represents hydrogen;
$R^4$ represents hydrogen;
X represents oxygen or sulphur;
n represents the integer 0 or 1;
Ar represents phenyl which is optionally mono-, di-, tri-, tetra- or pentasubstituted, or 2-pyridyl which is optionally mono-, di-, tri- or tetra- substituted, substituents on the phenyl or 2-pyridyl being cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentchloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a radical $-S(O)_m-R^5$,
wherein
$R^5$ represents amino, methylamino, ethylamino, dimethylamino, diethylamino, fluorodichloromethyl, difluoromethyl, tetrafluoroethyl, trichloroethyl, trichloromethyl, trifluoromethyl, methyl or ethyl and
m represents the integer 0, 1 or 2, and
Het represents

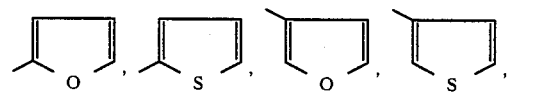
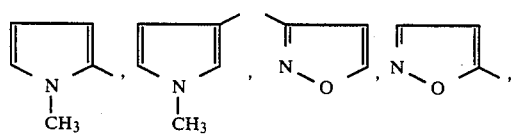
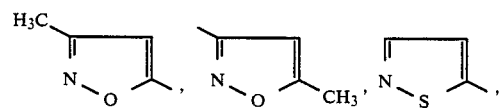
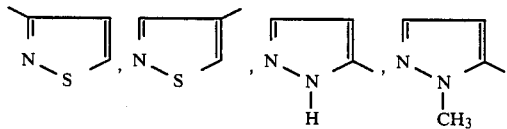
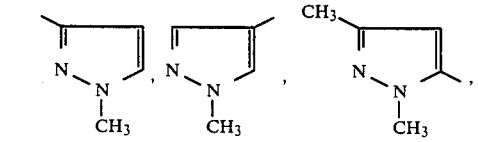
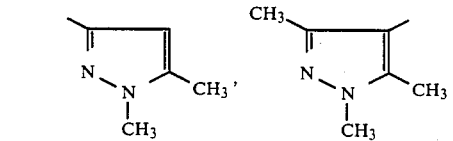

-continued

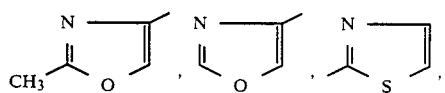
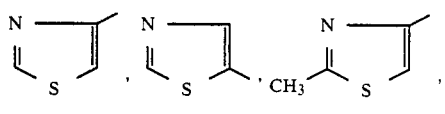
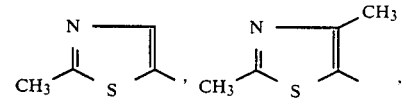
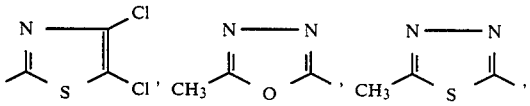
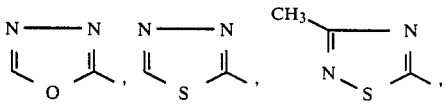
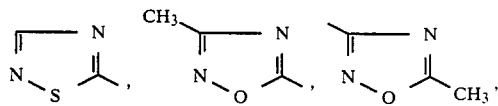
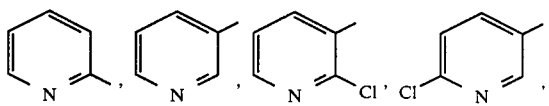
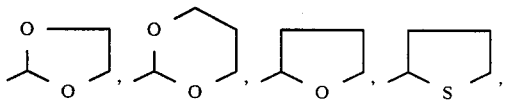
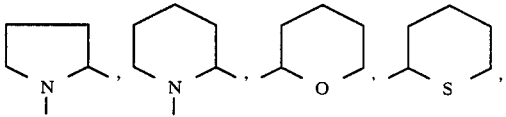
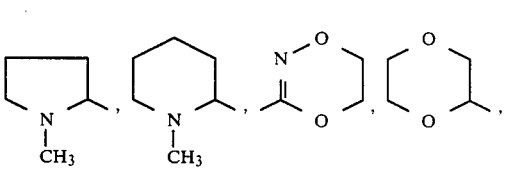
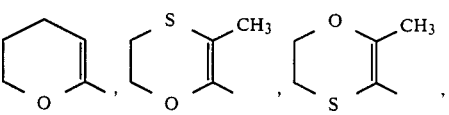
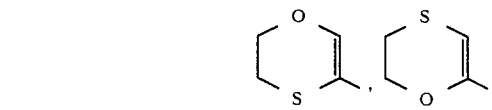

5. A compound according to claim 1, wherein such compound is 1-(2,6-dichloro-4-trifluoromethylphenyl)-4-nitro-5-(2-tetrahydrofuroyl)-aminopyrazole of the formula

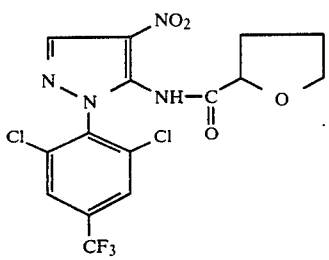

6. A compound according to claim 1, wherein such compound is 1-(2,6-dichloro-4-trifluoromethylphenyl)-4-nitro-5-(2-furoyl)-aminopyrazole of the formula

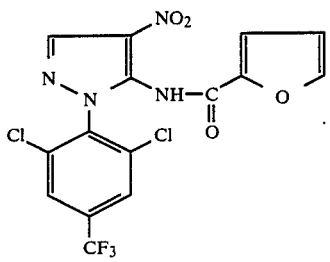

7. A compound according to claim 1, wherein such compound is 1-(2,3,5,6-tetrafluoro-4-trifluoromethylphenyl)-4-nitro-5-(2-tetrahydrofuroyl)-aminopyrazole of the formula

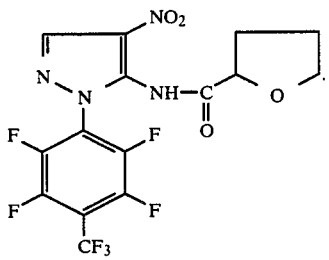

8. A compound according to claim 1, wherein such compound is 1-(2,6-dichloro-3,5-difluoro-4-trifluoromethylphenyl)-4-nitro-5-(2-tetrahydrofuroyl)-aminopyrazole of the formula

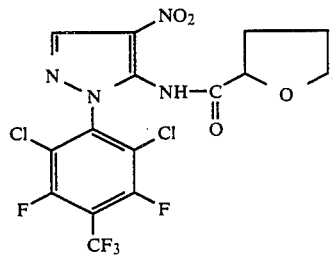

9. A compound according to claim 1, wherein such compound is 1-(2,3,6-trichloro-4-trifluoromethylphenyl)-4-nitro-5-(2-tetrahydrofuroyl)-aminopyrazole of the formula

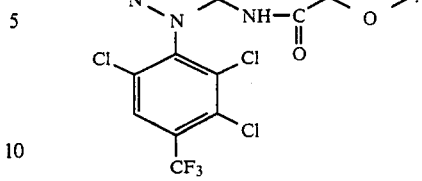

10. A compound according to claim 1, wherein such compound is 1-(2,6-dichloro-4-trifluoromethylmercaptophenyl)-4-nitro-5-(2-tetrahydrofuroyl)-aminopyrazole of the formula

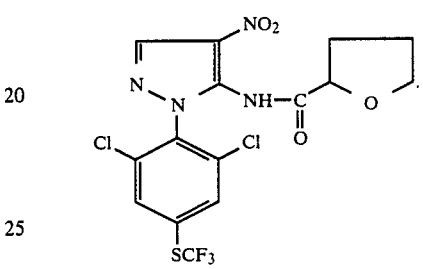

11. A herbicidal or plant growth regulating composition comprising a herbicidal or plant growth regulating effective amount of a 5-acylamino-pyrazole derivative according to claim 1 and a diluent.

12. A method of combating unwanted vegetation which comprises applying to such vegetation or to a locus from which it is desired to exclude such vegetation a herbicidally effective amount of a 5-acylaminopyrazole derivative according to claim 1.

13. The method according to claim 12 wherein such compound is
1-(2,6-dichloro-4-trifluoromethylphenyl)-4-nitro-5-(2-tetrahydrofuroyl)-aminopyrazole,
1-(2,6-dichloro-4-trifluoromethylphenyl)-4-nitro-5-(2-furoyl)-aminopyrazole,
1-(2,3,5,6-tetrafluoro-4-trifluoromethylphenyl)-4-nitro-5-(2-tetrahydrofuroyl)-aminopyrazole,
1-(2,6-dichloro-3,5-difluoro-4-trifluoromethylphenyl)-4-nitro-5-(2-tetrahydrofuroyl)-aminopyrazole,
1-(2,3,6-trichloro-4-trifluoromethylphenyl)-4-nitro-5-(2-tetrahydrofuroyl)-aminopyrazole or
1-(2,6-dichloro-4-trifluoromethylmercaptophenyl)-4-nitro-5-(2-tetrahydrofuroyl)-aminopyrazole.

14. A method regulating the growth of plants which comprises applying to such plants or to a locus in which such plants are growing or are to be grown a plant growth regulating effective amount of a 5-acylaminopyrazole derivative according to claim 1.

15. A method according to claim 14 wherein such compound is
1-(2,6-dichloro-4-trifluoromethylphenyl)-4-nitro-5-(2-tetrahydrofuroyl)-aminopyrazole,
1-(2,6-dichloro-4-trifluoromethylphenyl)-4-nitro-5-(2-furoyl)-aminopyrazole,
1-(2,3,5,6-tetrafluoro-4-trifluoromethylphenyl)-4-nitro-5-(2-tetrahydrofuroyl)-aminopyrazole,
1-(2,6-dichloro-3,5-difluoro-4-trifluoromethylphenyl)-4-nitro-5-(2-tetrahydrofuroyl)-aminopyrazole,
1-(2,3,6-trichloro-4-trifluoromethylphenyl)-4-nitro-5-(2-tetrahydrofuroyl-aminopyrazole or
1-(2,6-dichloro-4-trifluoromethylmercaptophenyl)-4-nitro-5-(2-tetrahydrofuroyl)-aminopyrazole.

* * * * *

UNITED STATES PATENT AND TRADEMARK OFFICE
CERTIFICATE OF CORRECTION

PATENT NO. : 4,772,309
DATED : September 20, 1988
INVENTOR(S) : Jörg Stetter, et al Page 1 of 3

It is certified that error appears in the above-identified patent and that said Letters Patent is hereby corrected as shown below:

| | |
|---|---|
| Col. 7, line 32 | Delete "chained" and substitute --chain-- |
| Col. 7, line 43 | After "mono-," delete "or" |
| Col. 31, line 6 | Bottom left of formula delete 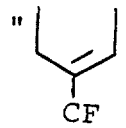 and substitute 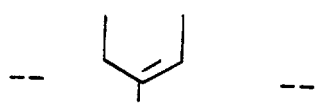 |
| Col. 38, line 49 | After "salts" delete "or" and substitute --of-- |
| Col. 39, line 7 | Correct spelling of --chloroacetanilide-- |
| Col. 39, line 18 | Delete "yloxy" and substitute --yl-oxy-- |
| Col. 39, line 57 | Delete "plants" and substitute --plant-- |
| Col. 54, lines 13-30 | Delete "Ar represents... 0, 1 or 2;" |
| Col. 54, line 54 | After "claim 1," insert --in which $R^1$ represents hydrogen, nitro, chlorine or bromine; $R^2$ represents hydrogen, or represents straight-chain or branched alkyl with 1 to 8 carbon atoms, or represents straight-chain or branched alkenyl or alkinyl with in each case 3 to 6 carbon atoms; $R^3$ represents hydrogen or methyl; $R^4$ represents hydrogen or methyl; X represents oxygen or sulfur; n represents the integer 0 or 1; |

UNITED STATES PATENT AND TRADEMARK OFFICE
CERTIFICATE OF CORRECTION

PATENT NO. : 4,772,309

DATED : September 20, 1988

Page 2 of 3

INVENTOR(S) : Jörg Stetter, et al

It is certified that error appears in the above-identified patent and that said Letters Patent is hereby corrected as shown below:

> Ar represents phenyl which is optionally mono-, di-, tri-, tetra- or pentasubstituted, or represents pyridyl optionally mono-, di-, tri- or tetrasubstituted, substituents on the phenyl or pyridyl being cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, difluorochloromethyl, difluorochloroethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, tri-

UNITED STATES PATENT AND TRADEMARK OFFICE
CERTIFICATE OF CORRECTION

PATENT NO. : 4,772,309
DATED : September 20, 1988
INVENTOR(S) : Jörg Stetter, et al Page 3 of 3

It is certified that error appears in the above-identified patent and that said Letters Patent is hereby corrected as shown below:

fluorochloroethoxy, trifluoroethoxy,--

Signed and Sealed this

Fourth Day of July, 1989

Attest:

DONALD J. QUIGG

Attesting Officer            Commissioner of Patents and Trademarks